(12) United States Patent
Benni

(10) Patent No.: US 11,454,589 B2
(45) Date of Patent: Sep. 27, 2022

(54) METHOD AND APPARATUS FOR NON-INVASIVELY MEASURING CIRCULATORY HEMOGLOBIN

(71) Applicant: Edwards Lifescienecs Corporation, Irvine, CA (US)

(72) Inventor: Paul B. Benni, Acton, MA (US)

(73) Assignee: Edwards Lifesciences Corporation, Irvine, CA (US)

( * ) Notice: Subject to any disclaimer, the term of this patent is extended or adjusted under 35 U.S.C. 154(b) by 543 days.

(21) Appl. No.: 16/593,223

(22) Filed: Oct. 4, 2019

(65) Prior Publication Data

US 2020/0033258 A1 Jan. 30, 2020

Related U.S. Application Data

(63) Continuation of application No. PCT/US2018/026140, filed on Apr. 4, 2018.

(60) Provisional application No. 62/481,398, filed on Apr. 4, 2017.

(51) Int. Cl.
| | |
|---|---|
| *A61B 5/1455* | (2006.01) |
| *G01N 21/359* | (2014.01) |
| *A61B 5/145* | (2006.01) |
| *A61B 5/00* | (2006.01) |
| *G01N 21/49* | (2006.01) |
| *A61B 5/1495* | (2006.01) |
| *G01N 21/27* | (2006.01) |

(52) U.S. Cl.
CPC ......... *G01N 21/359* (2013.01); *A61B 5/1455* (2013.01); *A61B 5/14542* (2013.01); *A61B 5/6814* (2013.01); *G01N 21/49* (2013.01); *A61B 5/0077* (2013.01); *A61B 5/1495* (2013.01); *A61B 5/14546* (2013.01); *G01N 21/274* (2013.01)

(58) Field of Classification Search
CPC . A61B 5/1455; A61B 5/14551; A61B 5/6814; A61B 5/14546; A61B 5/1495
See application file for complete search history.

(56) References Cited

U.S. PATENT DOCUMENTS

| | | | |
|---|---|---|---|
| 5,101,825 A * | 4/1992 | Gravenstein | ....... A61B 5/14535 600/326 |
| 5,729,333 A * | 3/1998 | Osten | ................. A61B 5/14535 356/39 |
| 6,456,862 B2 | 9/2002 | Benni | |
| 7,072,701 B2 | 7/2006 | Chen et al. | |
| 8,078,250 B2 | 12/2011 | Chen et al. | |
| 8,396,526 B2 | 3/2013 | Benni | |

(Continued)

*Primary Examiner* — Eric F Winakur

(74) *Attorney, Agent, or Firm* — Jessica Anne Hudak

(57) ABSTRACT

A method and apparatus of non-invasively determining a blood circulatory hemoglobin value for a subject using a near-infrared spectrophotometric (NIRS) sensing device is provided. The method includes: a) non-invasively sensing tissue of the subject using the NIRS sensing device at about a time T1, and determining at least one NIRS tissue totalHb value; b) acquiring at least one circulatory blood sample from the subject at about the time T1; c) determining at least one blood circulatory THb value; d) calibrating the NIRS sensing device using the at least one blood circulatory THb value and the at least one NIRS tissue TotalHb value; and e) determining at least one blood circulatory hemoglobin value using the calibrated NIRS sensing device and the at least one NIRS tissue totalHb value.

18 Claims, 6 Drawing Sheets

(56) References Cited

U.S. PATENT DOCUMENTS

| | | |
|---|---|---|
| 8,428,674 B2 | 4/2013 | Duffy et al. |
| 9,988,873 B2 | 6/2018 | Reddy |
| 2007/0060810 A1* | 3/2007 | Higgins ............ A61B 5/14535 600/328 |
| 2013/0165757 A1* | 6/2013 | Huiku ................ A61B 5/14535 600/323 |

* cited by examiner

METHOD AND APPARATUS FOR NON-INVASIVELY MEASURING CIRCULATORY HEMOGLOBIN

RELATED APPLICATIONS

This application describes similar subject matter and claims priority based on U.S. Provisional Patent Application No. 62/481,398, filed Apr. 4, 2017, United States International Application Serial No. PCT/US2018/026140, filed Apr. 4, 2018, the complete disclosures of which are hereby incorporated herein in their entireties.

BACKGROUND

1. Technical Field

This invention relates to methods and apparatus for determining blood circulatory hemoglobin values in general, and to non-invasive methods and apparatus for determining blood circulatory hemoglobin values in particular.

2. Background Information

The molecule that carries the oxygen in the blood is hemoglobin. Oxygenated hemoglobin is called oxyhemoglobin ($HbO_2$) and deoxygenated hemoglobin is deoxyhemoglobin (Hb). In some instances, blood may contain other types of hemoglobin (e.g., carboxyhemoglobin (COHb), methemoglobin (MetHb), etc.), but typically in relatively small amounts. The term "total hemoglobin" as used herein, therefore, refers to the sum of $HbO_2$ and Hb, and is proportional to relative blood volume changes, provided that the hematocrit or hemoglobin concentration of the blood is unchanged. The mammalian cardiovascular system consists of a blood pumping mechanism (the heart), a blood transportation system (blood vessels), and a blood oxygenation system (the lungs). Blood oxygenated by the lungs passes through the heart and is pumped into the arterial vascular system. Under normal conditions, oxygenated arterial blood consists predominately of $HbO_2$. Large arterial blood vessels branch off into smaller branches called arterioles, which profuse throughout biological tissue. The arterioles branch off into capillaries, the smallest blood vessels. In the capillaries, oxygen carried by hemoglobin is transported to the cells in the tissue, resulting in the release of oxygen molecules ($HbO_2 \rightarrow Hb$). Under normal conditions, only a fraction of the $HbO_2$ molecules give up oxygen to the tissue, depending on the cellular metabolic need. The capillaries then combine together into venuoles, the beginning of the venous circulatory system. Venuoles then combine into larger blood vessels called veins. The veins further combine and return to the heart, and then venous blood is pumped to the lungs. In the lungs, deoxygenated hemoglobin Hb collects oxygen becoming $HbO_2$ again and the circulatory process is repeated.

Near-infrared spectroscopy (NIRS) is an optical spectrophotometric method of continually monitoring tissue parameters (e.g., oxygen saturation, hemoglobin levels, etc.) that does not require pulsatile blood volume to calculate parameters of clinical value. NIRS spectroscopy is based on the principle that light in the near-infrared range (700 to 1,000 nm) can pass easily through skin, bone and other tissues where it encounters hemoglobin located mainly within micro-circulation passages (e.g., capillaries, arterioles, and venuoles). Hemoglobin exposed to light in the near infra-red range has specific absorption spectra that varies depending on its oxidation state (i.e., oxyhemoglobin ($HbO_2$) and deoxyhemoglobin (Hb) each act as a distinct chromophore). By using light sources that transmit near-infrared light at specific different wavelengths, and measuring changes in transmitted or reflected light attenuation, concentration changes of the oxyhemoglobin ($HbO_2$) and deoxyhemoglobin (Hb) within tissue can be monitored, as well as oxygen saturation. U.S. Pat. Nos. 6,456,862; 7,072,701; 8,078,250, all describe NIRS spectroscopy devices and methods, each of which is hereby incorporated by reference in its entirety.

Near Infrared spectroscopy (NIRS) oximeters can provide a non-invasively determined total hemoglobin value for a subject's tissue. As will be described below, the total hemoglobin of tissue is proportional to relative blood volume within the sensed tissue (which volume may change), provided that the hematocrit or hemoglobin concentration of the blood is unchanged. Using an optical based sensor placed on the skin of a subject, a NIRS tissue oximeter can be used to interrogate tissue with different wavelengths of light (e.g., emit light into and detect light emanating from the tissue), and then process the detected light to calculate a total hemoglobin value for the tissue, and if desired also a tissue oxygen saturation ($StO_2$) value. For example, a sensor portion of a NIRS oximeter placed on the forehead of a subject may be used to spectrophotometrically interrogate a subject's brain tissue and thereafter determine total hemoglobin and $StO_2$ values for the subject's brain tissue.

Historically, circulatory blood hemoglobin values (i.e., a hemoglobin value representative of hemoglobin within circulatory blood) have been determined using an invasively drawn blood sample. The invasively drawn blood sample specimen may be analyzed using a CO-oximeter or a blood-gas analyzer. A CO-oximeter is a device that may be operated to measure one or more types of hemoglobin present within a blood specimen; e.g., $HbO_2$, Hb, carboxyhemoglobin (COHb), methemoglobin (MetHb), etc. Most CO-oximeters are spectrophotometric devices that may be operated to determine the presence and amount of the respective types of hemoglobin (e.g., $HbO_2$, Hb, COHb, MetHb, etc.) within the invasively drawn blood sample by measuring the absorption of light at specific wavelengths passing through the blood sample. The relative amounts of absorption at the different wavelengths enable a measurement of the respective types of hemoglobin present within the blood sample. Most blood-gas analyzers, in contrast, are electrochemical type analysis devices that use electrodes and changes in electrical current or potential to detect and measure constituents within the invasively drawn blood sample.

A primary difference between a prior art NIRS tissue oximeter and a CO-oximeter or a blood-gas analyzer is that the NIRS tissue oximeter is configured to determine a parameter value (e.g., hemoglobin, oxygen saturation, etc.) within tissue, whereas the CO-oximeter or blood-gas analyzer is configured to determine the same parameter value within a circulatory blood sample (i.e., an invasively collected blood sample). Using total hemoglobin as an example parameter, the total hemoglobin value determined within tissue using a prior art NIRS tissue oximeter can be affected by several different physiological parameters, including circulatory blood hemoglobin, hemoglobin concentration per volume of tissue, vasoreactivity, cardiac output, blood flow, partial pressure of carbon dioxide in arterial blood ($PaCO_2$), heart rate, blood volume, hematomas, hyperemia, etc. A total hemoglobin value of a circulatory blood sample determined using a CO-oximeter or a blood-gas analyzer will not be affected by these physiological parameters, but requires an invasive collection step.

SUMMARY

According to an aspect of the present disclosure, a method of non-invasively determining a blood circulatory hemoglobin value for a subject using a near-infrared spectrophotometric (NIRS) sensing device is provided. The method includes: a) non-invasively sensing tissue of the subject using the NIRS sensing device at about a time T1, and determining at least one NIRS tissue totalHb value based on the non-invasive sensing; b) acquiring at least one circulatory blood sample from the subject at about the time T1; c) determining at least one blood circulatory THb value of the acquired circulatory blood sample; d) calibrating the NIRS sensing device using the at least one blood circulatory THb value and the at least one NIRS tissue TotalHb value; and e) determining at least one blood circulatory hemoglobin value using the calibrated NIRS sensing device and the at least one NIRS tissue totalHb value.

According to another aspect of the present disclosure, a method of non-invasively determining a blood circulatory hemoglobin value for a subject using a near-infrared spectrophotometric (NIRS) sensing device is provided. The method includes: a) non-invasively sensing tissue of the subject using the NIRS sensing device at about a time T1, and determining at least one T1 NIRS tissue totalHb value based on the non-invasive sensing at about the time T1, and non-invasively sensing tissue of the subject using the NIRS sensing device at about a time T2, which time T2 is different than time T1, and determining at least one T2 NIRS tissue totalHb value based on the non-invasive sensing at about the time T2; b) acquiring at least one circulatory blood sample from the subject at about the time T1, and acquiring at least one circulatory blood sample from the subject at about the time T2; c) determining at least one T1 blood circulatory THb value of the circulatory blood sample acquired at the time T1, and determining at least one T2 blood circulatory THb value of the circulatory blood sample acquired at the time T2; d) calibrating the NIRS sensing device using the at least one T1 blood circulatory THb value, the at least one T1 NIRS tissue totalHb value, the at least one T2 blood circulatory THb value, and the at least one T2 NIRS tissue totalHb value; and e) determining at least one blood circulatory hemoglobin value using the calibrated NIRS sensing device and at least one NIRS tissue totalHb value.

According to another aspect of the present disclosure, a near-infrared spectrophotometric (NIRS) sensing device configured to non-invasively determine a blood circulatory hemoglobin value for a subject is provided. The device includes at least one transducer portion and a processor portion. The at least one transducer portion has at least one light source and a least one light detector. The processor portion is in communication with the at least one transducer portion. The processor portion includes at least one processor in communication with stored instructions, which instructions when executed cause the processor to: a) control the at least one transducer portion to non-invasively sense tissue of the subject using the NIRS sensing device at about a time T1, and determine at least one NIRS tissue totalHb value based on the non-invasive sensing; b) calibrate the NIRS sensing device using the at least one NIRS tissue TotalHb value, and at least one blood circulatory THb value of a circulatory blood sample acquired at about the time T1; and c) determine at least one blood circulatory hemoglobin value using the calibrated NIRS sensing device and the at least one NIRS tissue totalHb value.

According to another aspect of the present disclosure, a near-infrared spectrophotometric (NIRS) sensing device configured to non-invasively determine a blood circulatory hemoglobin value for a subject is provided. The device includes at least one transducer portion and a processing portion. The at least one transducer portion has at least one light source and a least one light detector. The processor portion is in communication with the at least one transducer portion. The processor portion includes at least one processor in communication with stored instructions, which instructions when executed cause the processor to: a) control the at least one transducer portion to non-invasively sense tissue of the subject using the NIRS sensing device at about a time T1, and determine at least one T1 NIRS tissue totalHb value based on the non-invasive sensing at about the time T1, and to non-invasively sense tissue of the subject using the NIRS sensing device at about a time T2, which time T2 is different than time T1, and to determine at least one T2 NIRS tissue totalHb value based on the non-invasive sensing at about the time T2; b) calibrate the NIRS sensing device using the at least one T1 NIRS tissue TotalHb value, at least one T1 blood circulatory THb value of a circulatory blood sample acquired at about the time T1, the at least one T2 NIRS tissue TotalHb value, at least one T2 blood circulatory THb value of a circulatory blood sample acquired at about the time T2; and c) determine at least one blood circulatory hemoglobin value using the calibrated NIRS sensing device and at least one NIRS tissue totalHb value.

In any of the aspects or embodiments described above and herein, the at least one blood circulatory hemoglobin value may be a NIRS circulatory THb value.

In any of the aspects or embodiments described above and herein, the calibrating step may utilize empirical data.

In any of the aspects or embodiments described above and herein, the empirical data may include an empirical circulatory THb calibration slope.

In any of the aspects or embodiments described above and herein, the calibrating step may include determining a subject calibration intercept determined using the at least one blood circulatory THb value, the at least one NIRS tissue TotalHb value, and the empirical circulatory THb calibration slope.

In any of the aspects or embodiments described above and herein, the step of determining at least one blood circulatory hemoglobin value step may further utilize the empirical circulatory THb calibration slope and the subject calibration intercept.

In any of the aspects or embodiments described above and herein, the calibrating step may include determining a multi-point subject calibration intercept using the at least one T1 blood circulatory THb value, the at least one T1 NIRS tissue totalHb value, the at least one T2 blood circulatory THb value, and the at least one T2 NIRS tissue totalHb value.

In any of the aspects or embodiments described above and herein, the calibrating step may include determining an individual subject calibration slope using the at least one T1 blood circulatory THb value, the at least one T1 NIRS tissue totalHb value, the at least one T2 blood circulatory THb value, and the at least one T2 NIRS tissue totalHb value.

In any of the aspects or embodiments described above and herein, the step of determining at least one blood circulatory hemoglobin value, may further utilize the multi-point subject calibration intercept and the individual subject calibration slope.

In any of the aspects or embodiments described above and herein, the empirical data may include an empirical circulatory THb calibration slope, and the stored instructions may cause the processor to determine a subject calibration intercept determined using the at least one blood circulatory THb value, the at least one NIRS tissue TotalHb value, and the empirical circulatory THb calibration slope.

DETAILED DESCRIPTION

The present method and apparatus for noninvasively measuring circulatory hemoglobin utilizes a near infrared spectrophotometric (NIRS) sensing device 8 (sometimes referred to as a "NIRS oximeter") that includes one or more transducers 10 and a processing portion 12. Each transducer 10 is capable of being operated to transmit light signals into the tissue of a subject and to sense the transmitted light signals once they have passed through the subject's tissue via transmittance or reflectance. A variety of NIRS sensing device types can be modified according to aspects of the present disclosure, and aspects of the present disclosure are not therefore limited to any particular type of NIRS sensing device.

Figure 1:
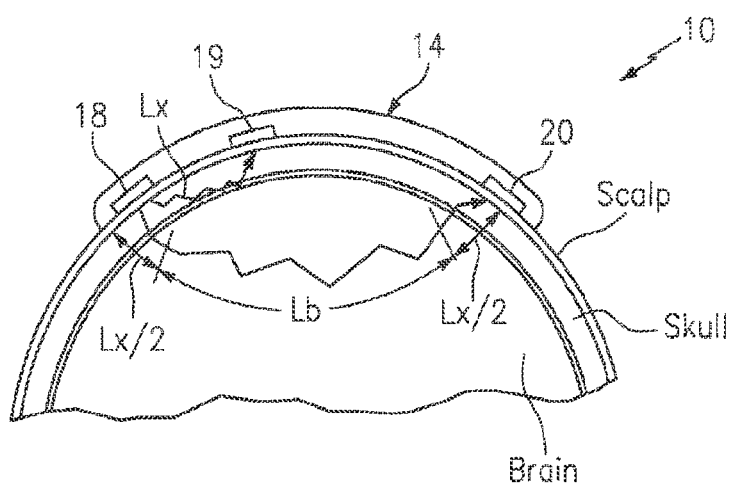
FIG. 1 is a diagrammatic representation of a NIRS sensor applied to a subject's head.
Figure 2:
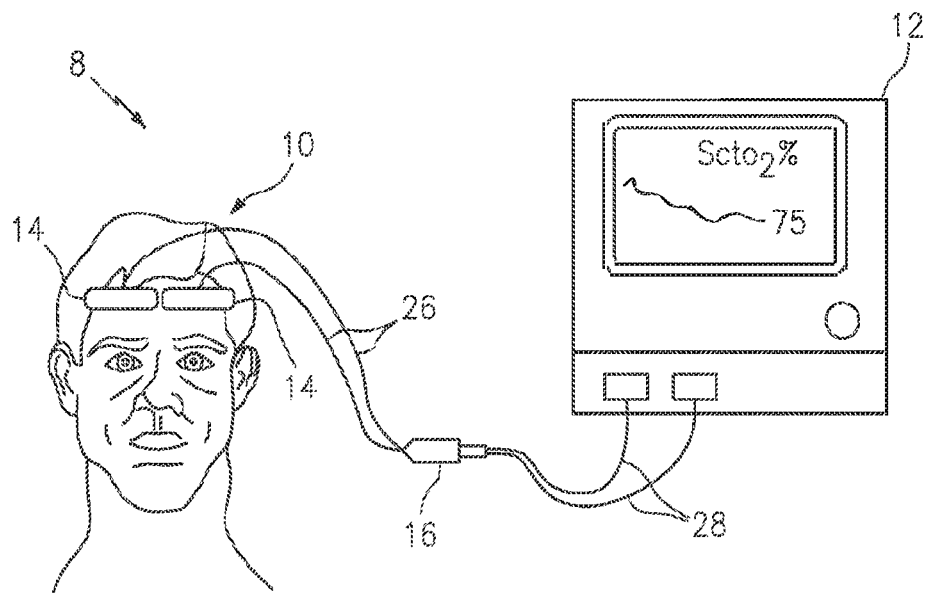
FIG. 2 is a diagrammatic representation of a NIRS sensing device.
Figure 3:
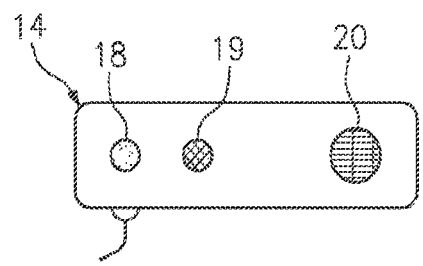
FIG. 3 is a diagrammatic representation of a transducer portion of a NIRS sensing device.

Referring to FIGS. 1-3, an example of an acceptable NIRS sensing device transducer 10 is shown. The transducer 10 includes an assembly housing 14, a connector housing 16. A connector cable 26 extends between each assembly housing 14 and the connector housing 16. One or more connector cables 28 extend between the connector housing 16 and the processing portion 12. The assembly housing 14 is typically a flexible structure that can be attached directly to a subject's body, and includes one or more light sources 18 and light detectors 19, 20. The light detectors 19, 20 may be described as a "near" detector (light detector 19) and a "far" detector (light detector 20), where the terms "near" and "far" indicate the relative distances from the light source 18. A disposable adhesive envelope or pad may be used to mount the housing 14 easily and securely to the subject's skin. The light sources 18 may be light emitting diodes ("LEDs") that emit light at a narrow spectral bandwidth at predetermined wavelengths. The light sources 18 are not, however, limited to LEDs. The light detectors 19, 20 each include one or more photodiodes, or other light detecting devices. The photodiodes are also operably connected to the processing portion 12 via the connector cables 26, 28. Non-limiting examples of acceptable NIRS sensing device transducers 10 are described in U.S. Pat. Nos. 9,988,873 and 8,428,674, both of which are commonly assigned to the assignee of the present application and both of which are hereby incorporated by reference in their entirety.

The processing portion 12 includes one or more processors that can be used to control the operations described in association with any of the computer-implemented method steps described herein. The processing portion may include additional components such as a memory device, a storage device, an input/output device, etc. One or more of the components may be interconnected using a system bus. The term "processor" as used herein may refer to any type of computing device, computational circuit, any type of process or processing circuit, including multiple processors, multicore CPUs, microprocessors, digital signal processors, microcontrollers, or the like, alone or in any combination thereof. The processor is capable of executing a series of instructions (e.g., instructions for implementing the method steps/algorithms described herein, controlling components such as the light sources 18 and light detectors 19, 20, etc.) that are stored in memory, including a non-transitory memory. The memory can include volatile memory and/or non-volatile memory, and may be a computer readable medium. In general, the storage device can include any non-transitory tangible media configured to store computer readable instructions. In some embodiments, the input/output device may include a keyboard, a pointing device, a touch screen, or the like. In some embodiments, the input/output device may include a display unit; e.g., for displaying graphical user interfaces and/or data. Features of the present disclosure may be implemented in digital electronic circuitry, in computer hardware, firmware, or any combination thereof. The features can be implemented in a computer program product tangibly embodied in an information carrier, e.g., in a machine-readable storage device, for execution by a processor. The processing portion is adapted to control operation of the light sources and process light signals provided directly or indirectly from the light detectors as described herein.

The processing portion 12 is adapted to determine blood oxygen parameter values, including oxygen saturation values (that may be referred to as "$SnO_2$", "$StO_2$", "$SctO_2$", "$CrSO_2$", "$rSO_2$", etc.) and hemoglobin concentration values (e.g., $HbO_2$ and Hb). U.S. Pat. Nos. 6,456,862; 7,072,701; and 8,396,526 (each of which is hereby incorporated by reference in its entirety) each disclose methods for spectrophotometric blood monitoring. The methods of determining blood parameters disclosed in U.S. Pat. Nos. 6,456,862 and 7,072,701 represent acceptable examples of determining a subject-independent blood parameter values. Aspects of the present disclosure may include, but are not limited to including, those specific methods. The method disclosed in U.S. Pat. No. 8,396,526 represents an acceptable example of a method of determining a blood parameter value that accounts for the specific physical characteristics of the particular subject's tissue being sensed; i.e., a method that builds upon a subject-independent algorithm such as those disclosed in U.S. Pat. Nos. 6,456,862 and 7,072,701 to make it subject-dependent. Aspects of the present disclosure may include, but are not limited to, the specific methods described in U.S. Pat. No. 8,396,526. The present disclosure described herein provides methods and techniques for modifying such methods, or for use with other NIRS methodologies, to enable a determination of a NIRS circulatory THb value.

According to the present disclosure, the present apparatus and method are configured to permit a determination of a NIRS circulatory THb value; i.e., the stored instructions that are utilized by the processing portion 12 include instructions for determining a NIRS circulatory THb value using a non-invasive NIRS tissue TotalHb value determined from sensing a subject's tissue, at least one blood circulatory total hemoglobin ("blood circulatory THb") value determined from an invasively collected blood sample (e.g., the blood circulatory THb value determined by a CO-oximeter or a blood-gas analyzer), and one or more calibration parameters.

The at least one blood circulatory THb value may be determined, for example, using known CO-oximeter or blood-gas analyzer technologies, or comparable technologies. As indicated above, CO-oximeters and blood-gas analyzers, and their ability to determine a blood circulatory THb value for an invasively collected blood sample are well known, and no further description is required herein for enablement purposes. The present disclosure is not limited to determining the blood circulatory THb value of the invasively collected blood sample by any particular technology. Preferably, the blood sample used to determine the at least one blood circulatory THb value is collected at or about the same time as the non-invasive NIRS sensing is performed that yields the NIRS tissue THb value.

Figure 4:
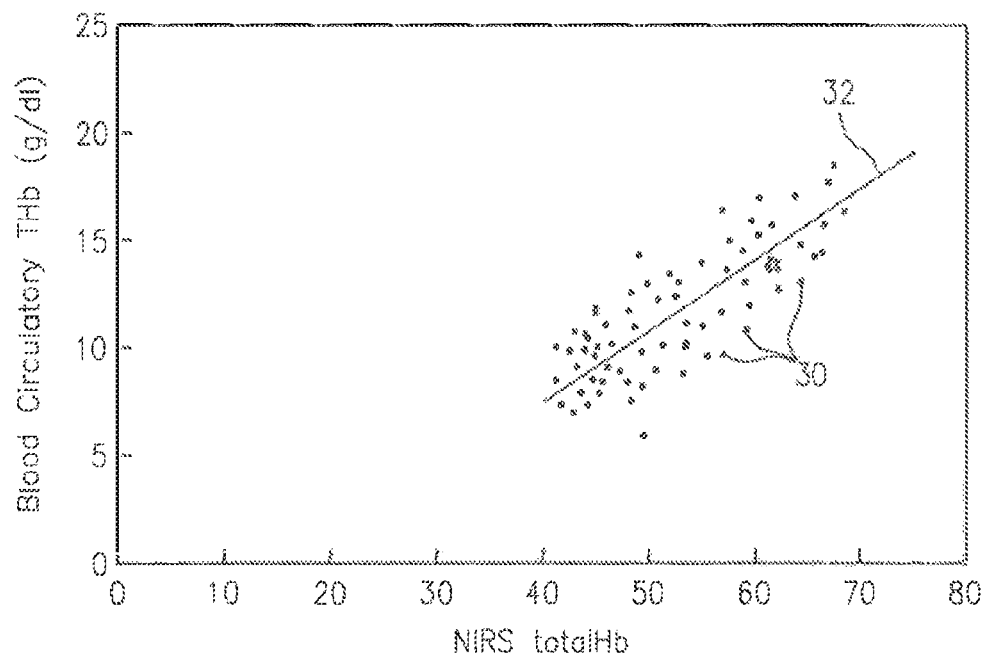
FIG. 4 is a scatter plot of data points shown on a chart having a Y-axis representing Blood Circulatory values and an X-axis showing NIRS tissue TotalHb values, and a trend line determined from the data points.

The one or more calibration parameters portion of the stored instructions includes data and/or instructions representative of empirical data collected from a clinically sufficient population of subjects. For example, the empirical data may include a clinically significant number of data sets, each data set including a NIRS tissue TotalHb value and a corresponding blood circulatory THb value from a subject. As described above, the NIRS tissue TotalHb value within each data set may be determined by using a noninvasive NIRS sensing device to sense the subject's tissue (e.g., interrogating the tissue with light at particular wavelengths and collecting the light to determine attenuation of the light). The NIRS tissue TotalHb value may be the sum of $HbO_2$ and Hb values determined within the sensed volume of tissue; e.g., see methodology described in U.S. Pat. Nos. 6,456,862; 7,072,701; and 8,396,526. As stated above, however, the present disclosure is not limited to determining a NIRS tissue TotalHb value in the manner described in the aforesaid patents, and may be determined via a different methodology. The corresponding blood circulatory THb value is determined from an invasively collected blood sample, which is preferably collected at the same time or at substantially the same time as the noninvasive NIRS sensing is performed. The corresponding blood circulatory THb value may be determined using a CO-oximeter or a blood-gas analyzer. This process is repeated until a clinically sufficient number of data sets is collected from a clinically sufficient population of subjects. Each data set can be plotted as a single data point 30 on a scatter plot (e.g., a chart having a Y-axis representing Blood Circulatory values and an X-axis showing NIRS tissue TotalHb values; See FIG. 4) and a trend line 32 (sometimes referred to as a "best-fit" line) can be determined from the data points 30, which trend line 32 has a slope value and an intercept value. A linear regression technique may be used to define the trend line 30, slope value, and intercept value. The slope value may be referred to as an Empirical Circulatory TotalHb Calibration Slope; i.e., a calibration parameter.

Figure 5:
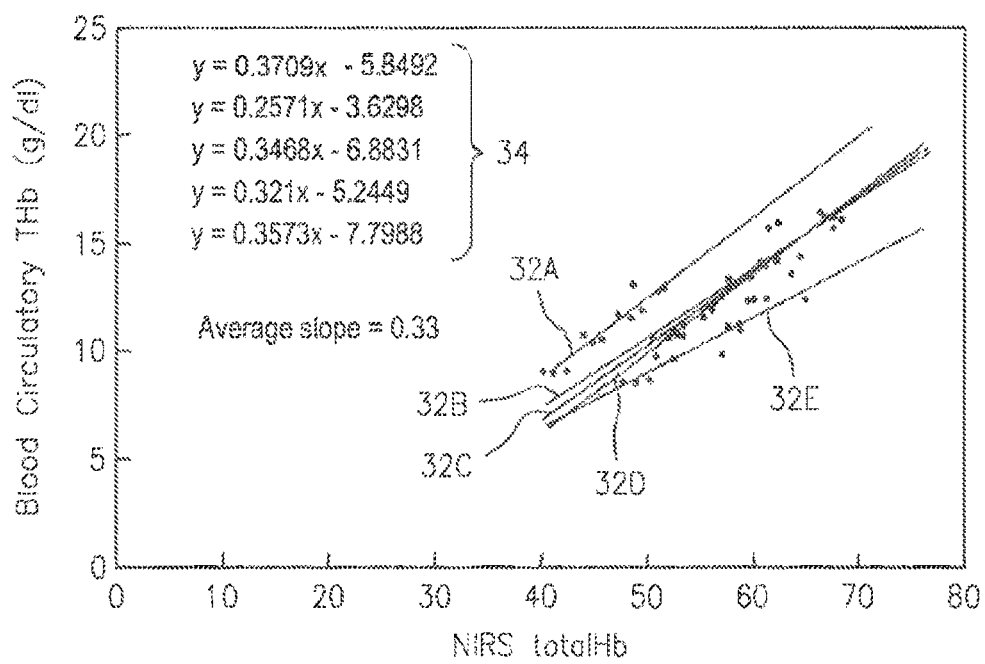
FIG. 5 is a scatter plot of data points shown on a chart having a Y-axis representing Blood Circulatory values and an X-axis showing NIRS tissue TotalHb values. The data includes a plurality data sets from different subjects, each data set containing a plurality of data points collected during a hemodilution protocol. A trend line is fit to each data set.

In some embodiments, the empirical data may include a plurality of data sets collected from each subject while the subject is subjected to a stepwise hemodilution protocol. An example of an acceptable stepwise hemodilution protocol involves collecting a unit of blood from the subject and replacing the removed blood with a blood compatible intravenous fluid (e.g., Ringer's lactate solution, etc.) at each step of the protocol. The removal of blood and addition of the intravenous fluid dilutes the subject's blood, but helps to maintain the overall volume of the circulatory system. At each step within the hemodilution protocol, a NIRS tissue TotalHb value and a blood circulatory THb value are determined. Each data sets from a subject subjected to the hemodilution protocol may be plotted as a single point on a scatter plot (e.g., See FIG. 5). A trend line can be fit to the data points from that particular subject (e.g., by linear regression technique), and trend line slope value and an intercept value can be determined for each data set. FIG. 5 illustrates data points from five (5) different subjects, each subjected to a hemodilution protocol, and a trend line (32A, 32B, 32C, 32D, 32E) for each set of data points from the respective subject. Mathematical representations 34 of the trend lines 32A-32E are shown in FIG. 5, as well as an average slope value of the five different trend lines. The trend line slope value determined from the hemodilution protocol data from a particular subject may be referred to as an "Individual Subject Calibration Slope". A clinically acceptable number of the Individual Subject Calibration Slopes can subsequently be used to create a statistical representative slope value (e.g., a mean value with an acceptable standard deviation, an average value, etc.— shown in FIG. 5 as "average slope") that may be referred to as an "Empirical Circulatory THb Calibration Slope" value. The aforesaid Empirical Circulatory THb Calibration Slope value may be subsequently used as a calibration parameter for a given type of NIRS sensing device, such as the type NIRS sensing device used to create the empirical data. An Empirical Circulatory THb Calibration Slope value (i.e., a calibration parameter) may be determined for each of a variety of types of NIRS sensing device (i.e., a calibration parameter specific to the particular type of NIRS sensing device, and/or with particular types of transducer types), by performing the above-described testing and collection of empirical data using the respective NIRS sensing device.

The Empirical Circulatory THb Calibration Slope may be stored within a non-transitory memory device in communication with the processing portion 12 of the NIRS sensing device to permit a conversion of a NIRS tissue TotalHb value into a NIRS circulatory THb value for clinical subjects subsequently monitored using the NIRS sensing device. For sake of clarity, although the subsequent clinical subjects may include subjects included in the "test subject calibration population", there is no requirement that subsequent clinical subjects have participated in the population of subjects used for to create the empirical data; i.e., the Empirical Circulatory THb Calibration Slope is not subject dependent.

A NIRS sensing device 8 according to the present disclosure may be configured to determine a NIRS circulatory THb value in a variety of different ways. For example, in a first embodiment of the present disclosure (which embodiment may be referred to as a "single-point" subject calibration; See FIGS. 6A and 7), a NIRS sensing device 8 empirically calibrated (via stored algorithm instructions) to include an Empirical Circulatory THb Calibration Slope as described above may be used to sense a subject to determine a NIRS tissue TotalHb. At or about the same time as the subject is sensed to determine the NIRS tissue TotalHb value, a blood sample is drawn from the subject. A blood circulatory THb value of the invasively drawn blood sample is determined using a CO-oximeter or a blood-gas analyzer (or by other means) as described above. This blood circulatory THb value is inputted into the NIRS monitor by a touchscreen keyboard or some other means. The NIRS circulatory THb value can be subsequently determined using the Empirical Circulatory THb Calibration Slope, the NIRS tissue TotalHb value, and the blood circulatory THb value by the processor of the NIRS monitor. For example, the determined blood circulatory THb value can be input into the calibrated NIRS sensing device 8. The processing portion 12 acting on the stored instructions can then be used to operate the processing portion to create a subject calibration intercept using the following equation:

Subject Calibration Intercept=Blood Circulatory
THb−(NIRS tissue Total*Hb*×Empirical Circulatory *THb* Calibration Slope)     (EQN. 1)

Figure 5A:
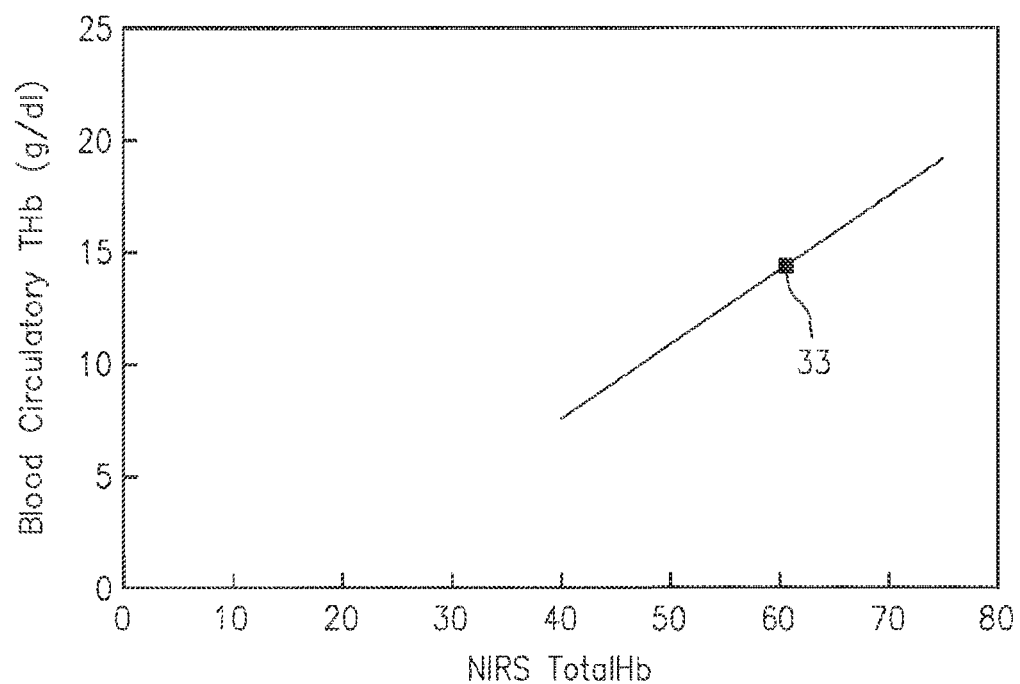
FIG. 5A is a scatter plot showing a single data point collected in a single-point subject calibration methodology shown on a chart having a Y-axis representing Blood Circulatory values and an X-axis showing NIRS tissue TotalHb values.

FIG. 5A illustrates a single data point 33 reflecting a respective blood circulatory THb value and a NIRS tissue TotalHb value plotted on a chart having a Y-axis representing Blood Circulatory values and an X-axis showing NIRS tissue TotalHb values. The Subject Calibration Intercept would typically be determined at a start time ($T_0$). Once the Subject Calibration Intercept is determined, the NIRS Circulatory THb can be determined using the following equation:

NIRS Circulatory *THb*=(NIRS tissue Total*Hb*×Empirical Circulatory *THb* calibration slope)+Subject Calibration Intercept     (EQN.2)

Figure 7:
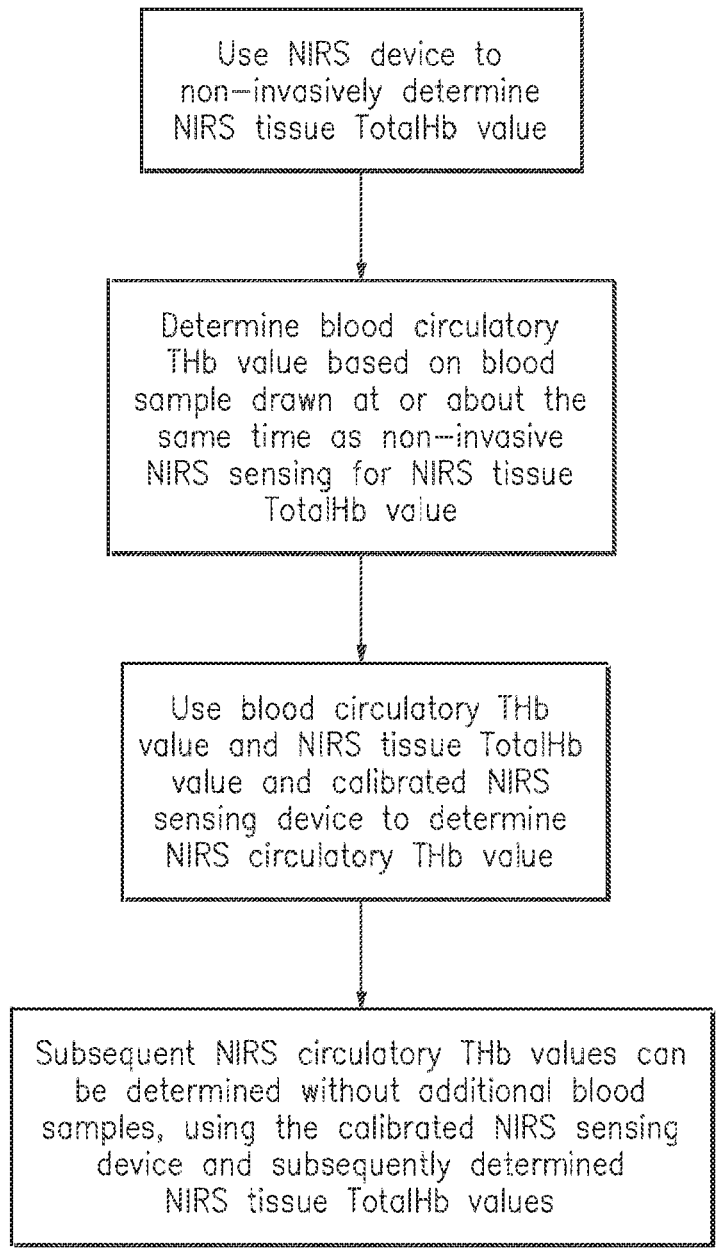
FIG. 7 is a flow chart describing steps in a single-point subject calibration methodology and subsequent data collection.

It should be noted that Equations 1 and 2 are non-limiting examples of mathematical expressions that can be used. Referring to FIG. 7, the NIRS Circulatory THb could then be determined at any time ("T") during monitoring of that particular subject using the calibrated NIRS sensing device (e.g., calibrated using the single-point subject calibration specific to the subject) at any time after initiation ($T>T_0$), without the need for a subsequent invasive circulatory blood sample.

Figure 6:
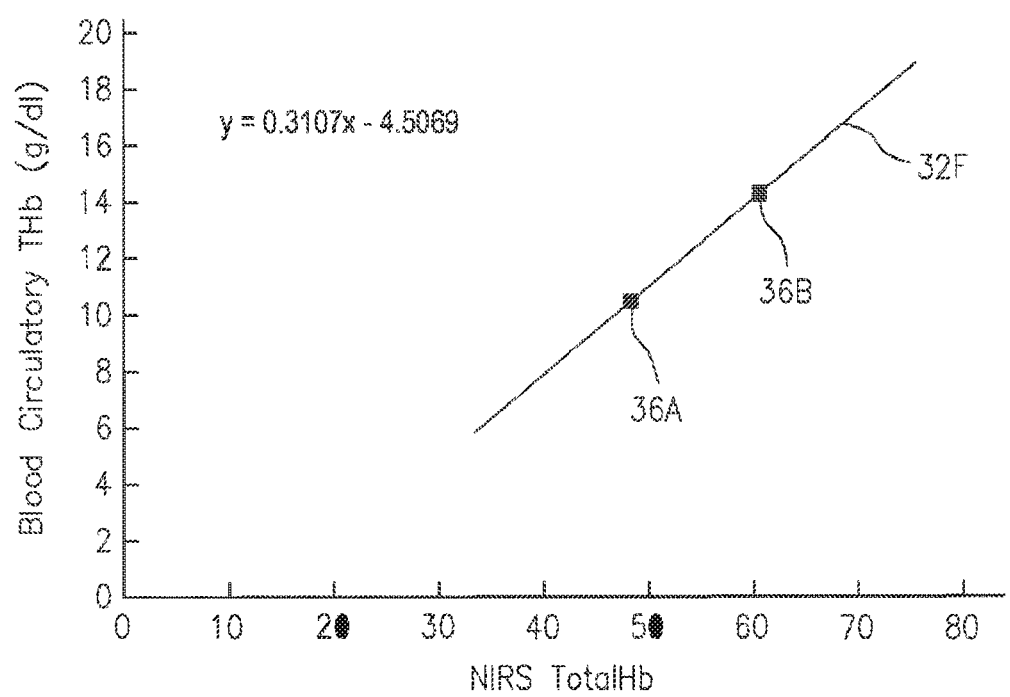
FIG. 6 is a scatter plot showing two data points collected in a multi-point subject calibration methodology shown on a chart having a Y-axis representing Blood Circulatory values and an X-axis showing NIRS tissue TotalHb values, and a trend line determined from the data points.
Figure 8:
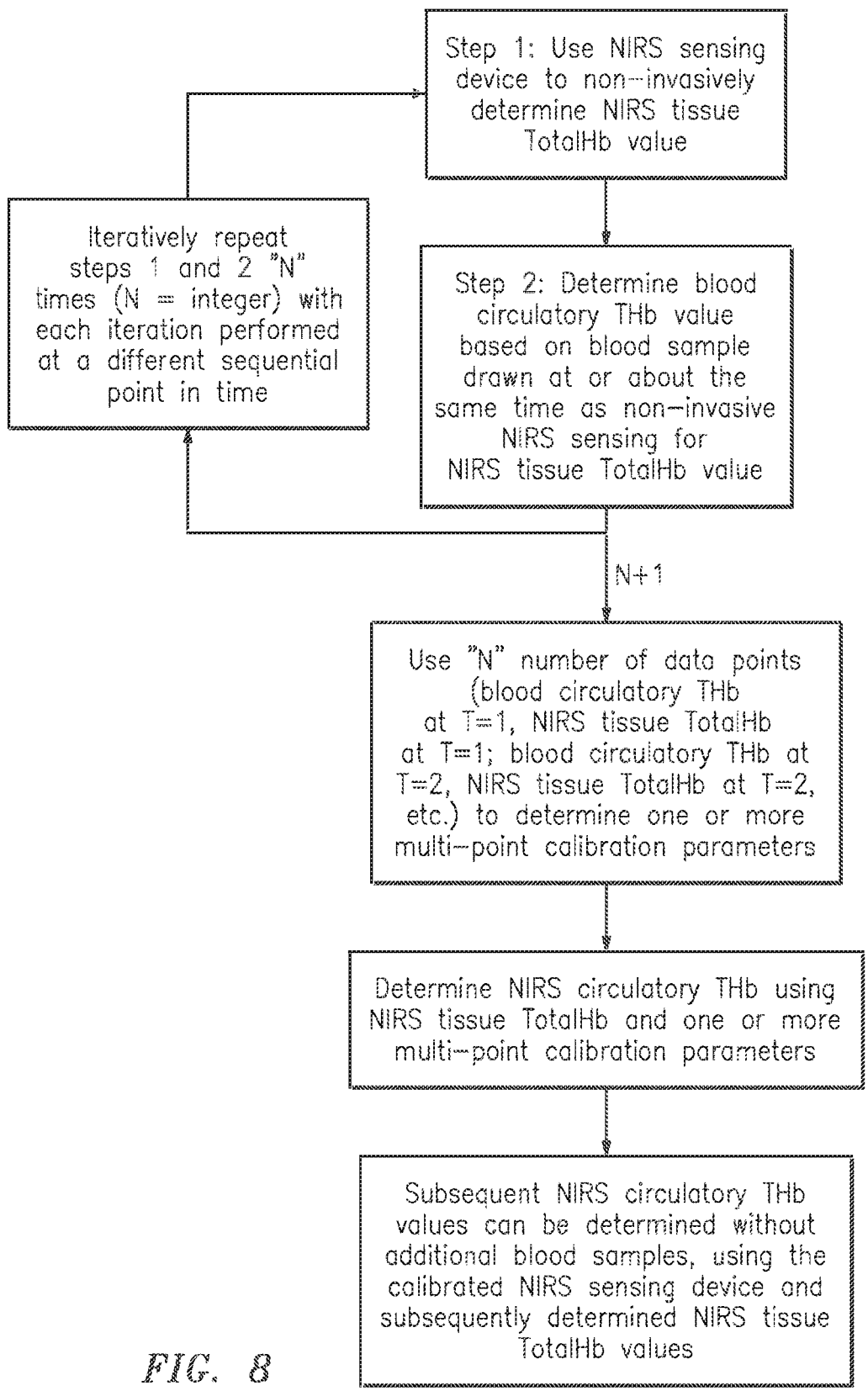
FIG. 8 is a flow chart describing steps in a multi-point subject calibration methodology and subsequent data collection.

In another embodiment (which embodiment may be referred to as a "multi-point" subject calibration; see FIG. 8), the NIRS sensing device (e.g., the processing portion) may be configured with stored algorithm instructions to permit the user to enter a plurality of blood circulatory THb values, each determined using a blood sample invasively collected during a period of time when the subject is noninvasively monitored using the NIRS sensing device, and each typically collected at a different point in time. For example, as shown in FIG. 6, a pair of data points 36A, 36B reflecting a respective blood circulatory THb value and a NIRS tissue TotalHb value are shown plotted on a chart having a Y-axis representing Blood Circulatory values and an X-axis showing NIRS tissue TotalHb values. The data used to produce a given data point 36A, 36B (e.g., blood sample, NIRS sensing) is collected at or about the same time, and each data point 36A, 36B reflects data collected at a different point in time; e.g., data for data point 36A collected at T1, and data collected for data point 36B collected at T2, where T1 is different than T2. These data points may be connected via a trend line 32F, and a slope and intercept value determined. The slope value and intercept value may respectively be referred to as an "Individual Subject Calibration Slope" and a "Multi-point Subject Calibration Intercept". Of course, if more than two data points are plotted (i.e., more than two blood samples are collected and the respective blood circulatory THb value and NIRS tissue TotalHb values determined), the trend line may be determined using a linear regression technique, or a simple slope equation, or the like.

A NIRS sensing device 8 now "calibrated" (via stored algorithm instructions) with the "Individual Subject Calibration Slope" and the "Multi-point Subject Calibration Intercept", may be used to determine a NIRS tissue TotalHb. A NIRS Circulatory THb can then be calculated, for example, with the following equation:

NIRS Circulatory *THb*=(NIRS tissue Total*Hb*×Individual Subject Calibration Slope)+Multi-point Subject Calibration Intercept     (EQN. 3)

It should be noted that Equation 3 is a non-limiting example of a mathematical expression that can be used. The NIRS Circulatory THb could then be determined at any time during monitoring of that particular subject using the calibrated NIRS sensing device at any time after the above described multi-point subject calibration, without the need for further invasive circulatory blood samples. This multi-point subject calibration method is particularly useful when there is a known or expected major change in circulatory total hemoglobin during the monitoring period, which often occurs, for example, when a subject undergoes a cardiac surgery with bypass and hemodilution. In many instances, the present multi-point subject calibration method will substantially improve the accuracy and precision of NIRS Circulatory THb measurements. It should be noted, that using the above described methodology of determining a NIRS circulatory THb value, which is based on multiple blood samples drawn from the subject being monitored, provides a NIRS circulatory THb value that more accurately reflects the circulatory hemoglobin level of that particular subject. Once the NIRS sensing device 8 is calibrated using the above described multi-point subject calibration methodology, a NIRS Circulatory THb can be determined at any time during monitoring of that particular subject without the need for a subsequent invasive circulatory blood sample.

Figure 9:
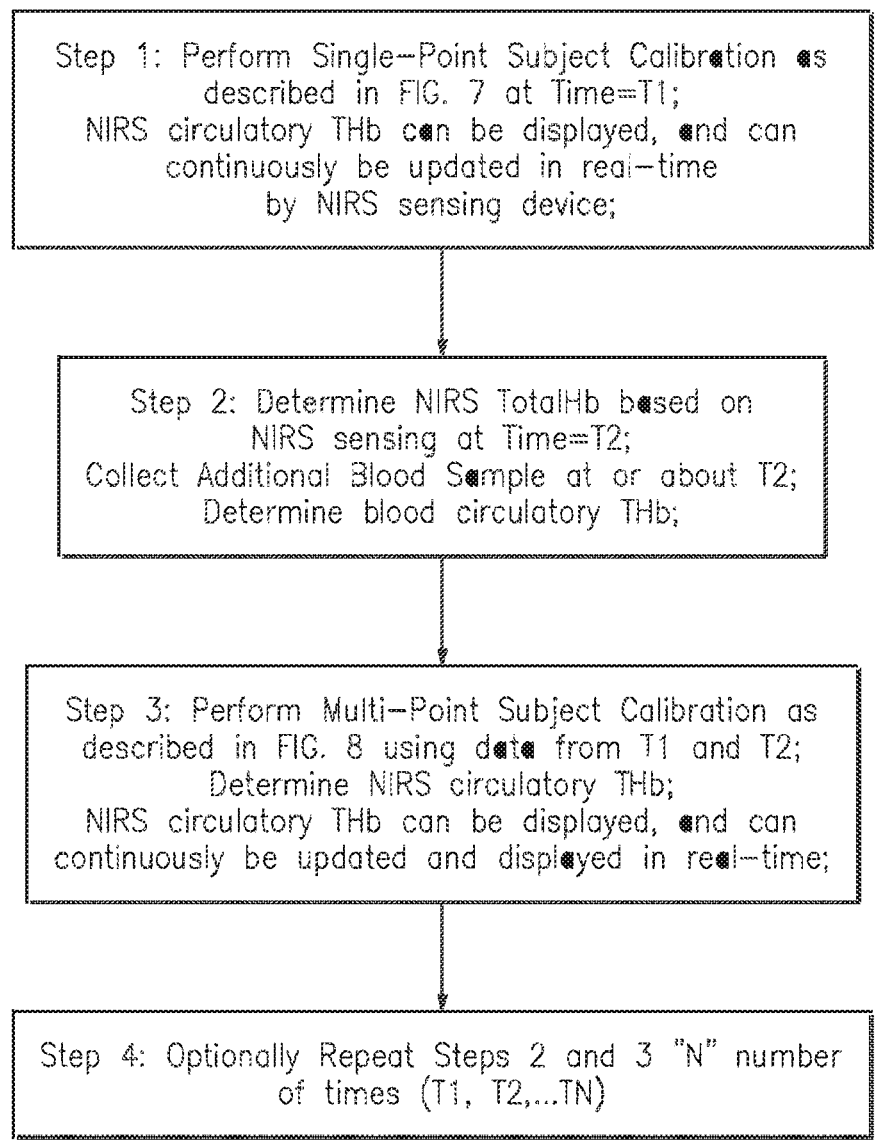
FIG. 9 is a flow chart describing steps in a sequential methodology that utilizes a single-point subject calibration methodology, subsequent multi-point subject calibration methodology, and subsequent data collection.

Referring to FIG. 9, a sequential application of the above described methodologies for determining a NIRS circulatory THb value can provide a desirable option to the clinician. As described above, a single data point analysis (e.g., based on a single NIRS tissue TotalHb value, and a single blood circulatory THb value determined from a single invasively drawn blood sample, which sample was drawn at or about the same time as the subject was sensed to determine the NIRS tissue TotalHb value) can be used to determine a NIRS circulatory THb value. This provides the advantage of NIRS circulatory THb being calculated immediately after the first blood sample THb value is inputted into the NIRS monitor. If the clinician desires to confirm the determined NIRS circulatory THb value at a later time, or suspects that an event has occurred that may have resulted in a change in the subject's circulatory total hemoglobin, then the clinician may draw another sample of blood to obtain a THb value to be inputted into the NIRS monitor to allow the monitor to prepare another data point analysis (e.g., determine a second NIRS tissue TotalHb value, and second blood circulatory THb value based on the second invasively drawn blood sample). The instructions stored within the processing portion 12 can then be used to prepare a multi-point subject analysis (e.g., as described above with respect to FIGS. 6 and 8, and Equation 3) using the first data point and the second data point. This process can be repeated as many times as desired. As stated above, the aforesaid multi-point subject methodology which utilizes multiple blood samples drawn from the subject being monitored can provide a NIRS circulatory THb value that more accurately reflects the circulatory hemoglobin level of that particular subject.

The methods and apparatus according to the present disclosure enable clinicians and other users to display circulatory THb values determined by non-invasive NIRS in real-time after one or more blood samples are drawn. Prior art methods (e.g., circulatory THb values determined by CO-oximeters and/or blood-gas analyzers) require a sample to be drawn and analysis of that sample every time data is desired. Once a NITS sensing device is calibrated as described herein, it is possible to provide accurate information in real-time and thereby enable clinicians and health officials to provide care base thereon.

While the invention has been described with reference to an exemplary embodiment(s), it will be understood by those skilled in the art that various changes may be made and equivalents may be substituted for elements thereof without departing from the scope of the invention. For example, the term "total hemoglobin" is described herein as being the sum of $HbO_2$ and Hb. The present disclosure contemplates embodiments wherein a total hemoglobin value may include contributions from one or more other types of hemoglobin; e.g., carboxyhemoglobin (COHb), methemoglobin (MetHb), etc. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims

What is claimed is:

1. A method of non-invasively determining a blood circulatory hemoglobin value for a subject using a near-infrared spectrophotometric (NIRS) sensing device, comprising:
   non-invasively sensing tissue of the subject using the NIRS sensing device at about a time T1, and determining at least one NIRS tissue totalHb value based on the non-invasive sensing;
   acquiring at least one circulatory blood sample from the subject at about the time T1;
   determining at least one blood circulatory THb value of the acquired circulatory blood sample;
   calibrating the NIRS sensing device using the at least one blood circulatory THb value and the at least one NIRS tissue TotalHb value;
   determining at least one blood circulatory hemoglobin value using the calibrated NIRS sensing device and at least one subsequent NIRS tissue totalHb value.

2. The method of claim 1, wherein the at least one blood circulatory hemoglobin value is a NIRS circulatory THb value.

3. The method of claim 2, wherein the calibrating step utilizes empirical data.

4. The method of claim 3, wherein the empirical data includes an empirical circulatory THb calibration slope.

5. The method of claim 4, wherein the calibrating step includes determining a subject calibration intercept determined using the at least one blood circulatory THb value, the at least one NIRS tissue TotalHb value, and the empirical circulatory THb calibration slope.

6. The method of claim 5, wherein the determining at least one blood circulatory hemoglobin value step further utilizes the empirical circulatory THb calibration slope and the subject calibration intercept.

7. A method of non-invasively determining a blood circulatory hemoglobin value for a subject using a near-infrared spectrophotometric (NIRS) sensing device, comprising:
   non-invasively sensing tissue of the subject using the NIRS sensing device at about a time T1, and determining at least one T1 NIRS tissue totalHb value based on the non-invasive sensing at about the time T1, and non-invasively sensing tissue of the subject using the NIRS sensing device at about a time T2, which time T2 is different than time T1, and determining at least one T2 NIRS tissue totalHb value based on the non-invasive sensing at about the time T2;
   acquiring at least one circulatory blood sample from the subject at about the time T1, and acquiring at least one circulatory blood sample from the subject at about the time T2;
   determining at least one T1 blood circulatory THb value of the circulatory blood sample acquired at the time T1, and determining at least one T2 blood circulatory THb value of the circulatory blood sample acquired at the time T2;
   calibrating the NIRS sensing device using the at least one T1 blood circulatory THb value, the at least one T1 NIRS tissue totalHb value, the at least one T2 blood circulatory THb value, and the at least one T2 NIRS tissue totalHb value; and
   determining at least one blood circulatory hemoglobin value using the calibrated NIRS sensing device and at least one subsequent NIRS tissue totalHb value.

8. The method of claim 7, wherein the at least one blood circulatory hemoglobin value is a NIRS circulatory THb value.

9. The method of claim 8, wherein the calibrating step utilizes empirical data.

10. The method of claim 9, wherein the empirical data includes an empirical circulatory THb calibration slope.

11. The method of claim 10, wherein the calibrating step includes determining a multi-point subject calibration intercept using the at least one T1 blood circulatory THb value, the at least one T1 NIRS tissue totalHb value, the at least one T2 blood circulatory THb value, and the at least one T2 NIRS tissue totalHb value.

12. The method of claim 11, wherein the calibrating step includes determining an individual subject calibration slope using the at least one T1 blood circulatory THb value, the at least one T1 NIRS tissue totalHb value, the at least one T2 blood circulatory THb value, and the at least one T2 NIRS tissue totalHb value.

13. The method of claim 12, wherein the step of determining at least one blood circulatory hemoglobin value, further utilizes the multi-point subject calibration intercept and the individual subject calibration slope.

14. A near-infrared spectrophotometric (NIRS) sensing device configured to non-invasively determine a blood circulatory hemoglobin value for a subject, comprising:

at least one transducer portion having at least one light source and a least one light detector;

a processor portion in communication with the at least one transducer portion, the processor portion including at least one processor in communication with stored instructions, which instructions when executed cause the processor to:

control the at least one transducer portion to non-invasively sense tissue of the subject using the NIRS sensing device at about a time T1, and determine at least one NIRS tissue totalHb value based on the non-invasive sensing;

calibrate the NIRS sensing device using the at least one NIRS tissue TotalHb value, and at least one blood circulatory THb value of a circulatory blood sample acquired at about the time T1; and determine at least one blood circulatory hemoglobin value using the calibrated NIRS sensing device and at least one subsequent NIRS tissue totalHb value.

15. The device of claim 14, wherein the at least one blood circulatory hemoglobin value is a NIRS circulatory THb value.

16. The device of claim 15, wherein the stored instructions include empirical data and the NIRS sensing device is calibrated utilizing the empirical data.

17. The device of claim 16, wherein the empirical data includes an empirical circulatory THb calibration slope, and the stored instructions cause the processor to determine a subject calibration intercept determined using the at least one blood circulatory THb value, the at least one NIRS tissue TotalHb value, and the empirical circulatory THb calibration slope.

18. A near-infrared spectrophotometric (NIRS) sensing device configured to non-invasively determine a blood circulatory hemoglobin value for a subject, comprising:

at least one transducer portion having at least one light source and a least one light detector;

a processor portion in communication with the at least one transducer portion, the processor portion including at least one processor in communication with stored instructions, which instructions when executed cause the processor to:

control the at least one transducer portion to non-invasively sense tissue of the subject using the NIRS sensing device at about a time T1, and determine at least one T1 NIRS tissue totalHb value based on the non-invasive sensing at about the time T1, and to non-invasively sense tissue of the subject using the NIRS sensing device at about a time T2, which time T2 is different than time T1, and to determine at least one T2 NIRS tissue totalHb value based on the non-invasive sensing at about the time T2;

calibrate the NIRS sensing device using the at least one T1 NIRS tissue TotalHb value, at least one T1 blood circulatory THb value of a circulatory blood sample acquired at about the time T1, the at least one T2 NIRS tissue TotalHb value, at least one T2 blood circulatory THb value of a circulatory blood sample acquired at about the time T2; and determine at least one blood circulatory hemoglobin value using the calibrated NIRS sensing device and at least one subsequent NIRS tissue totalHb value.

* * * * *